United States Patent [19]

Nishii et al.

[11] Patent Number: 5,795,984

[45] Date of Patent: Aug. 18, 1998

[54] PROCESS FOR PRODUCING ISATOIC ANHYDRIDES

[75] Inventors: Shinji Nishii; Masashi Komatsu; Hiroshi Ueda, all of Osaka, Japan

[73] Assignee: Sumitomo Chemical Company Limited, Osaka, Japan

[21] Appl. No.: 773,357

[22] Filed: Dec. 26, 1996

[30] Foreign Application Priority Data

Dec. 26, 1995 [JP] Japan ................................. 7-339145
Apr. 26, 1996 [JP] Japan ................................. 8-107469

[51] Int. Cl.⁶ ............................................. C07D 265/14
[52] U.S. Cl. ........................................................ 544/94
[58] Field of Search .......................................... 544/94

[56] References Cited

U.S. PATENT DOCUMENTS

| | | | |
|---|---|---|---|
| 4,159,330 | 6/1979 | Doria et al. | 544/94 |
| 4,261,996 | 4/1981 | Sircar | 544/250 |
| 4,268,511 | 5/1981 | Baronnet et al. | 544/94 |
| 4,364,316 | 12/1982 | Kruse | 544/94 |
| 4,524,203 | 6/1985 | Walter et al. | 544/94 |
| 4,734,419 | 3/1988 | Hashimoto et al. | 514/259 |
| 4,883,800 | 11/1989 | Hashimoto et al. | 514/259 |

FOREIGN PATENT DOCUMENTS

| | | |
|---|---|---|
| 0012051 | 6/1980 | European Pat. Off. |
| 0621262 | 10/1994 | European Pat. Off. |
| 2436781 | 4/1980 | France . |
| 1949014 | 4/1971 | Germany . |
| 1-25767 | 5/1989 | Japan . |

OTHER PUBLICATIONS

S.M. Gadekar et al., "Some Halogenated 1,2,3-Benzotriazin-4(3H)ones", *The Journal of Organic Chemistry*, vol. 26, No. 2, Feb. 24, 1961, pp. 613–615.

Primary Examiner—Donald G. Daus
Attorney, Agent, or Firm—Sughrue, Mion, Zinn, Macpeak & Seas, PLLC

[57] ABSTRACT

A process for producing isatoic anhydrides of the formula (II):

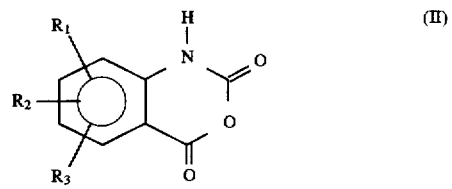

which comprises reacting an anthranilic acid of formula (I):

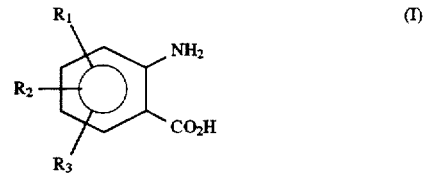

or a salt thereof with phosgene using a mixed solvent of water and an organic solvent miscible with water and inert to the reaction; conducting the reaction in the coexistence of an alkylpyridinium salt in an aqueous solvent; or using a mixed solvent of water and a specific amount of an organic solvent substantially immiscible with water and inert to the reaction.

5 Claims, No Drawings

PROCESS FOR PRODUCING ISATOIC ANHYDRIDES

The present invention relates to a process for producing isatoic anhydrides. More particularly, it relates to a process for producing isatoic anhydrides using corresponding anthranilic acid or a salt thereof and phosgene.

Isatoic anhydrides are useful as an intermediate of an antiphlogistic, a remedy for diabetic complication, etc as described in U.S. Pat. Nos. 4,734,419 and 4,883,800. As the production process, for example, there is known that isatoic anhydrides are produced by using corresponding anthranilic acid or a salt thereof and phosgene in the presence of a water solvent (J. Org. Chem., 26, 613 (1961)).

However, the above process using water as the solvent had an industrial problem that the reaction mixture changes into a whipped cream state and, therefore, a volume efficiency of a reactor is very low and an yield of the objective product is not satisfactory.

The present inventors have intensively studied about the process for producing isatoic anhydrides so as to solve these drawbacks.

As a result, it has been found that, by using a mixed solvent consisting of water and an organic solvent which is miscible with water and is inert to the reaction, in place of water conventionally used as the reaction solvent, it becomes possible to inhibit the formation of whipped cream mass from the reaction mixture, thereby remarkably improving not only the volume efficiency of the reactor but also the yield The present inventors have also found, by coexisting a specific compound, an alkylpyridinium salt, in the reaction, inhibition of the formation of whipped cream mass from the reaction mixture, that is, the remarkable improvment of volume efficiency of the reactor as well as of the yield, can be attained.

The present inventors have further found that, by using a mixed solvent consisting of water and a specific amount of an organic solvent which is substantially immiscible with water and is inert to the reaction in place of water conventionally used as the reaction solvent, it is also possible to solve the above-mentioned problems of the conventional method.

Thus, the present invention has been accomplished.

That is, the present invention provides a process for producing isatoic anhydrides represented by the formula (II):

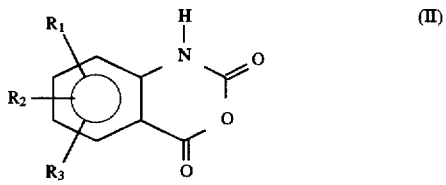

wherein $R_1$ and $R_2$ independently indicate a hydrogen atom, a halogen atom, a nitro group, a lower alkyl group which is optionally substituted with a halogen atom, an aralkyl group which is optionally substituted with a halogen atom, an alkoxy group which is optionally substituted with a halogen atom, an alkoxycarbonyl group which is optionally substituted with a halogen atom, an acyloxy group or $XNR_4R_5$ (X is a direct bond, a lower alkylene group or a carbonyl group or a carbonyloxy group in which the nitrogen atom is attached to carbonyl provided that, when X is a direct bond or a lower alkylene group, $R_4$ and $R_5$ independently indicate a lower alkyl group or N, $R_4$ and $R_5$ may form a five- or six-membered heterocycle which optionally contain another hetero atom and, when X is a carbonyl group, $R_4$ and $R_5$ independently indicate a hydrogen atom or a lower alkyl group or N, $R_4$ and $R_5$ may form a five- or six-membered heterocycle which optionally contain another hetero atom and further, when containing another hetero atom, said hetero atom may be substituted); and $R_3$ is a hydrogen atom, a halogen atom, a nitro group, a lower alkyl group which is optionally substituted with a halogen atom, an aralkyl group which is optionally substituted with a halogen atom, an alkoxy group which is optionally substituted with a halogen atom or an alkoxycarbonyl group which is optionally substituted with a halogen atom, which comprises reacting phosgene and an anthranilic acid represented by the formula (I):

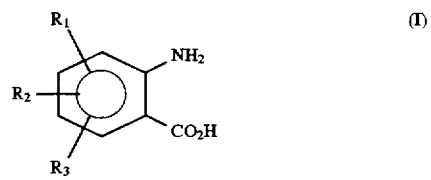

wherein $R_1$, $R_2$ and $R_3$ are as defined above, or a salt thereof using a mixed solvent comprising water and an organic solvent which is miscible with water and inert to the reaction.

In this specification, including the accompanying claims, unless otherwise specified; alkyl groups and moieties may be straight or branched chain and generally contain from 1 to 6 carbon atoms; alkylene groups may be straight or branched chain and generally contain from 1 to 6 carbon atoms; and heteroatoms are generally selected from oxygen, sulphur and nitrogen.

The present invention also provides a process for producing an isatoic anhydride compound of the formula (II) which comprises reacting phosgene and an anthranilic acid compound of the formula (I) or a salt thereof in the coexistence of an alkylpyridinium salt.

The present invention further provides a process for producing an isatoic anhydride compound of the formula (II) which comprises reacting phosgene and an anthranilic acid compound of the formula (I) or a salt thereof using a mixed solvent comprising water and an organic solvent which is substantially immiscible with water and inert to the reaction, the amount of the organic solvent being in a range of 1.5–20 fold by weight or more with respect to the amount of an anthranilic acid compound of the formula (I) or a salt thereof.

Hereinafter, the present invention will be described in detail.

The substituents $R_1$ and $R_2$ in anthranilic acids (I) as the raw material of the present invention independently indicate a hydrogen atom, a halogen atom, a nitro group, a lower alkyl group which is optionally substituted with a halogen atom, an aralkyl group which is optionally substituted with a halogen atom, an alkoxy group which is optionally substituted with a halogen atom, an alkoxycarbonyl group which is optionally substituted with a halogen atom, an acyloxy group or $XNR_4R_5$ (X is a direct bond, a lower alkylene group or a carbonyl group provided that, when X is a direct bond or a lower alkylene group, $R_4$ and $R_5$ independently indicate a lower alkyl group or N, $R_4$ and $R_5$ may form a five- or six-membered heterocycle which optionally contain another hetero atom and, when X is a carbonyl group, $R_4$ and $R_5$ independently indicate a hydrogen atom or a lower alkyl group or N, $R_4$ and $R_5$ may form a five- or six-membered heterocycle which optionally contain another hetero atom and further, when containing another hetero atom, said hetero atom can be substituted); and $R_3$ is a hydrogen atom, a halogen atom, a nitro group, a lower alkyl group which is optionally substituted with a halogen atom, an aralkyl group which is optionally substituted with a halogen atom, an alkoxy group which is optionally substituted with a halogen atom or an alkoxycarbonyl group which is optionally substituted with a halogen atom.

Examples of the halogen atom include chlorine, bromine and fluorine.

Examples of the lower alkyl group which is optionally substituted with the halogen atom include lower alkyl group such as methyl, ethyl, propyl, i-propyl, butyl, i-butyl, t-butyl, pentyl, i-pentyl and hexyl; monohalo lower alkyl group such as chloromethyl, bromomethyl and chloropropyl; dihalo lower alkyl group such as 1,2-dichloroethyl, 1,2-dibromoethyl and 2,2-dichloroethyl; and 2,4-dibromobenzyl; and trihalo lower a such as trifluoromethyl.

Examples of the aralkyl group which is optionally substituted with the halogen atom include benzyl, phenylethyl, 4-chlorobenzyl, 2,4-dichlorobenzyl and 2,4-dibromobenzyl. dichlorobenzyl and 2,4-dibromobenzyl.

Examples of the alkoxy group which is optionally substituted with the halogen atom include lower alkoxy group such as methoxy, ethoxy, propoxy, i-propoxy, butoxy, i-butoxy, t-butoxy, pentyloxy, i-pentyloxy, hexyloxy, etc.; and lower alkoxy group substituted with the halogen atom, such as chloromethoxy, bromomethoxy, 1-, 2-chloroethoxy, 1-, 2-, 3-chloropropoxy, dichloromethoxy, dibromoethoxy, 1,2-dichloroethoxy, 2,2-dichloroethoxy and trifluoromethoxy.

Examples of the alkoxycarbonyl group which is optionally substituted with the halogen atom include the same carbonyl group having the alkoxy group which is optionally substituted with the halogen atom as described above.

Examples of the acyloxy group include lower alkylcarbonyloxy group such as acetoxy, propionyloxy, butyryloxy, i-butyryloxy, valeryloxy, i-valeryloxy and pivaloyloxy, and arylcarbonyloxy group such as benzoyloxy.

Examples of the lower alkylene group in $XNR_4R_5$ include methylene, dimethylene, trimethylene and tetramethylene. Examples of $R_4$ and $R_5$ as 3 the lower alkyl group in $NR_4R_5$ include the same lower alkyl group as described above. Specific examples thereof include dimethylamino, diethylamino, dipropylamino and dibutylamino.

Specific examples of a five- or six-membered heterocycle formed by N, $R_4$ and $R_5$ in case that N, $R_4$ and $R_5$ in $NR_4R_5$ form a heterocycle which optionally have another hetero atom are pyrrolyl, 2H,4H-pyrrolyl, pyrrolidino, pyrazolyl, piperidino, morpholino and imidazolyl.

When another hetero atom is N, N can have a substituent. Examples of the substituent include a lower alkyl group which is optionally substituted with halogen as described above, an aralkyl group which is optionally substituted with halogen as described above, aralkyl group substituted with lower alkoxy, a phenylcarbonyl group which is optionally substituted with a lower alkoxy group and a phenylcarbonylalkyl group, e.g. 3-phenylcarbonylpropyl.

Typical examples of the anthranilic acids (I) include anthranilic acid, 3-,4-,5-,6-chloroanthranilic acid, 3-,4-,5-,6-bromoanthranilic acid, 3-,4-,5-,6-fluoroanthranilic acid, 3,4-3,5-,3,6-,4,5-,5,6-dichloroanthranilic acid, 3,4-3,5-,3,6-,4,5-,5,6-dibromoanthranilic acid, 3,4-, 3,5-,3,6-,4,5-,5,6-difluoroanthranilic acid, 3-bromo-4-chloroanthranilic acid, 3-bromo-5-chloroanthranilic acid, 3-bromo-6-chloroanthranilic acid, 4-bromo-3-chloroanthranilic acid, 4-bromo-5-chloroanthranilic acid, 4-bromo-6-chloroanthranilic acid, 5-bromo-3-chloroanthranilic acid, 5-bromo-4-chloroanthranilic acid, 5-bromo-6-chloranthranilic acid, 3-chloranthranilic acid, 6-bromo-4-chloroanthranilic acid, 6-bromo-5-chloroanthranilic acid, 3-chloro-4-fluoroanthranilic acid, 3-bromo-4-fluoroanthranilic acid, 3,4,5-,3,4,6-,3,5,6-,4,5,6-trichloroanthranilic acid, 3,4,5-,3,4,6-,3,5,6-,4,5,6-tribromoanthranilic acid, 3,4,5-,3,4,6-,3,5,6-,4,5,6-trifluoroanthranilic acid, 3,4,5-, 3,4,6-,4,5,6-trifluoroanthranilic acid, 3-,4-,5-,6-nitroanthranilic acid, 3-,4-,5-,6-methylanthranilic acid, 3-,4-,5-,6-ethylanthranilic acid, 3-,4-,5-,6-propylanthranilic acid, 3-,4-,5-,6-i-propylanthranilic acid, 3-,4-,5-,6-methoxycarbonylanthranilic acid, 3-,4-,5-,6-ethoxycarbonylanthranilic acid, 3-,4-,5-,6-propoxycarbonylanthranilic acid, 3-,4-,5-,6-i-propoxycarbonylanthranilic acid, 3-,4-,5-,6-butoxycarbonylanthranilic acid, 3-,4-,5-,6-(chloromethoxy)anthranilic acid, 3-,4-,5-,6-(bromomethoxy)anthranilic acid, 3-,4-,5-,6-(1-chloroethoxy)anthranilic acid 3-,4-,5-,6-(2-chloroethoxy)anthranilic acid, 3-,4-,5-,6-(1-chloropropoxy)anthranilic acid, 3-,4-,5-,6-(2-chloropropoxy)anthranilic acid, 3-,4-,5-,6-(3-chloropropoxy)anthranilic acid, 3-,4-,5-,6-dichloromethoxy)anthranilic acid, 3-,4-,5-,6-dibromomethoxy)anthranilic acid, 3-,4-,5-,6-(trifluoromethoxy)anthranilic acid, 3-,4-,5-,6-chloromethoxycarbonyl)anthranilic acid, 3-,4-,5-,6-(bromomethoxycarbonyl)anthranilic acid, 3-,4-,5-,6-(1-chloroethoxycarbonyl)anthranilic acid, 3-,4-,5-,6-(2-chloroethoxycarbonyl)anthranilic acid, 3-,4-,5-,6-(1-chloropropoxycarbonyl)anthranilic acid, 3-,4-,5-,6-(dichloromethoxycarbonyl)anthranilic acid, 3-,4-,5-,6-(dibromomethoxycarbonyl)anthranilic acid, 3-,4-,5-,6-(1,2-dichloromethoxycarbonyl)anthranilic acid, 3-,4-,5-,6(2,2-dichloromethoxycarbonyl)anthranilic acid, 3-,4-,5-,6-(trifluromethoxycarbonyl)anthranilic acid, 3-,4-,5-,6-chloromethylanthranilic acid, 3-,4-,5-,6-bromomethylanthranilic acid, 3-,4-,5-,6-(1-)chloroethyl)anthranilic acid 3-,4-,5-,6-(2-chloroethyl)anthranilic acid, 4-,5-,6- (dichloromethyl)anthranilic acid 3-,4-,5-,6-(1,2-chloroethyl)anthranilic acid, 3-,4-,5-,6-(2,2-dichloroethyl) anthranilic acid, 3,4-dimethylanthranilic acid, 3,4-diethylanthranilic acid, 3-benzylanthranilic acid, 3-(2-phenylethyl)anthranilic acid, 3-(4-chlorobenzyl)anthranilic acid, 3-(2,4-dichlorobenzyl)anthranilic acid, 3-(2,4-dibromobenzyl)anthranilic acid, 3-methoxyanthranilic acid, 3-ethoxyanthranilic acid, 3-propoxyanthranilic acid, 3-i-propoxyanthranilic acid, 4,5-dimethoxyanthranilic acid, 5,6-dimethoxyanthranilic acid, 3,5-diethoxyanthranilic acid, 3,6-dipropoxyanthranilic acid, 3- (N-dimethylamino)anthranilic acid, 3-(N,N-diethylamino)anthranilic acid, 3-(N,N-dipropylamino)anthranilic acid, 3-(N,N-dibutylamino)anthranilic acid, 3-(1-pyrrolyl)anthranilic acid, 3-(1-imidazolyl)anthranilic acid, 3-(1-pyrazolyl)anthranilic acid, 3-(2H,4H-pyrrolyl)anthranilic acid, 3-(piperidino)anthranilic acid, 3-(morpholino)anthranilic acid, 3-(4-methylpiperidino)anthranilic acid, 3-(4-(chloromethyl)piperidino)anthranilic acid, 3-(4-benzylpiperidino)anthranilic acid, 3-(4-(3-methoxybenzyl)piperidino)anthranilic acid, 3-(4-(phenylcarbonylpiperidino)anthranilic acid, 5-(4-(3,4-dimethoxyphenylcarbonyl)piperidino)anthranilic acid, 3-(1-pyrrolylmethyl)anthranilic acid, 3-(morpholinomethyl) anthranilic acid, 4-((4-methylpiperidino)methyl)anthranilic acid, 5- (4-(3-)phenylcarbonylpropyl)piperidinocarbonyl) anthranilic acid, phenylcarbonylpropyl)piperidinocarbonyl)

anthranilic acid, 4,6-dimethyl-5-ethyloxycarbonylanthranilic acid, 3chloro5,6-dimethoxyanthranilic acid, acid, 3-(N,N-dimethylcarbamoyl)anthranilic acid, 4-(4-methylpiperidinocarboxy)anthranilic acid, 5-(4-benzylpiperidinocarboxy)anthranilic acid, 5-(4-(3-phenylcarbonylpropyl)piperidinocarboxy)anthranilic acid, 4,6-dimethyl-5-ethyloxycarbonylanthranilic acid, 3-chloro-5,6-dimethoxyanthranilic acid, 4-acetoxyanthranilic acid, 4-propionyloxyanthranilic acid, 4-butyryloxyanthranilic acid, 4-i-butyryloxyanthranilic acid, 4-valeryloxyanthranilic acid, 4-i-valeryloxyanthranilic acid, 4-pivaloyloxyanthranilic acid and 4-benzoyloxyanthranilic acid.

The anthranilic acids (I) can also be used in the form of a salt. Either the amino group or the carboxyl group may form a salt. Examples of the salt include hydrochloride salt, sodium salt and potassium salt.

The object of the present invention can be attained by using a mixed solvent consisting of water and an organic solvent which is miscible with water and is inert to the reaction in place of water as the reaction solvent. (Hereinafter this method is referred to as Method 1.) Examples of the organic solvent which is miscible with water and is inert to the reaction include cyclic others such as tetrahydrofuran, dioxane; and glymes such as ethylene glycol dimethyl ether and diethylene glycol dimethyl ether. Among them, cyclic ethers, particularly tetrahydrofuran, are preferred.

The proportion of the organic solvent in the mixed solvent varies depending on the kind of anthranilic acid, the raw material, and kind of isatoic anhydride, the product, but is normally from 1 to 99% by weight, preferably from 5 to 95% by weight, more preferably from 10 to 90% by weight, further more preferably from 10 to 50% by weight, based on the total amount of the mixed solvent.

When the proportion of the organic solvent is less than 1% by weight, the effect of inhibiting tho formation of whipped cream mass from the reaction mixture is liable to be lowered. Therefore, normally, not less than 1% by weight of the mixed solvent is used.

An amount of the mixed solvent used is normally from 1- to 20-fold amount by weight, preferably from 2- to 10-fold amount by weight, with respect to the amount of anthranilic acids.

The object of the present invention can also be attained by reacting the anthranilic acid compound of the formula (1) or a salt thereof with phosgene in the coexistence of an alkylpyridinium salt in an aqueous solvent. (Hereinafter this method is referred to as Method 2.) Examples of the alkylpyridinium salt include compounds represented by the following formula (III):

(III)

wherein $R_6$ indicates an alkyl group having 8–20 carbon atoms, $R_7$ indicates a hydrogen atom or a lower alkyl group and X indicates an anion.

Examples of the alkyl group having 8–20 carbon atoms as $R_6$ include n-octyl, 2-ethylhexyl, nonyl decyl, i-decyl, undecyl, lauryl, tridecyl, myristyl, palmityl, stearyl and eicosyl. Examples of the lower alkyl group as $R_7$ include methyl, ethyl, propyl, i-propyl, butyl and pentyl.

X includes, for example, halogen anions such as chloride and bromide, sulfonyloxy anions such as methanesulfonyloxy, benzenesulfonyloxy and p-toluenesulfonyloxy.

Typical examples of the alkylpyridinium salt include laurylpyridinium chloride, laurylpyridinium bromide, cetylpyridinium chloride, cetylpyridinium bromide, myristyl-γ-picolinium chloride and lauryl-γ-picolinium benzenesulfonate.

The alkylpyridinium salt is used usually in about 0.005–0.5 fold amount by weight, preferably about 0.01–0.2 fold amount by weight, more preferably about 0.05–0.2 fold amount by weight, with respect to the amount of anthranilic acid compound of the formula (I).

In method 2, water, the reaction solvent, is used usually in about 1–20 fold amount by weight, preferably about 2–10 fold amount by weight, with respect to the amount of anthranilic acid compound of formula (I).

Further, in Method 2, an organic solvent substantially immiscible with water and inert to the reaction may be co-used as the solvent.

Examples of the organic solvent include aromatic hydrocarbons such as benzene, toluene and xylene; halogenated hydrocarbons such as chlorobenzene, o-dichlorobenzene, m-dichlorobenzene, bromobenzene, dichloromethane, chloroform, carbon tetrachloride and 1,2-dichloroethane; and ethers such as ethylether and di-i-propylether. Among them, aromatic hydrocarbons, halogenated hydrocarbons and the like, particularly toluene, chlorobenzene and the like, are preferred.

In method 2, the amount of the organic solvent, when used, is usually about 0.01–1 fold by weight, preferably about 0.1–0.5 fold by weight, with respect to the amount of water.

The object of the present invention can also be attained by using a mixed solvent consisting of water and an organic solvent which is substantially immiscible with water and is inert to the reaction in place of water as the reaction solvent. (Hereinafter this method is referred to as Method 3.) The amount of the organic solvent is in a range of 1.5–20 fold by weight, preferably 2.0–10 fold by weight, with respect to the amount of an anthranilic acid compound of the formula (I) or a salt thereof.

Examples of the organic solvent include aromatic hydrocarbons such as benzene, toluene and xylene; halogenated hydrocarbons such as chlorobenzene, o-dichlorobenzene, m-dichlorobenzene, bromobenzene, dichloromethane, chloroform, carbon tetrachloride and 1,2-dichloroethane; and others such as ethylether and di-i-propylether. Among them, aromatic hydrocarbons, halogenated hydrocarbons and the like, particularly toluene, chlorobenzene and the like, are preferred.

In Method 1, Method 2 and Method 3, the anthranilic acids or a salt thereof is dissolved or dispersed in the reaction solvent and, thereafter, is reacted with phosgene. The reaction is normally carried out by introducing phosgene into a reactor while adjusting the pH of the reaction mixture to about 2 to 10, preferably from about 3 to 9, more preferably about 6 to 7. The reaction temperature is normally from 0° to 40° C., preferably from 0° to 20° C.

For adjusting the pH, an alkali is normally used. Examples of the alkali include alkali metal hydroxide such as sodium hydroxide and potassium hydroxide; alkaline earth metal hydroxide such as magnesium hydroxide, calcium hydroxide and barium hydroxide; alkali metal carbonate such as sodium carbonate and potassium carbonate; alkaline earth metal carbonate such as magnesium carbonate, calcium carbonate and barium carbonate; alkali metal hydrogencarbonate such as sodium hydrogencarbonate and potassium hydrogencarbonate; and alkaline earth metal oxide such as calcium oxide and barium oxide. Among them, sodium hydroxide, potassium hydroxide, calcium hydroxide, sodium carbonate, potassium carbonate, sodium hydrogencarbonate and calcium hydrogencarbonate are preferably used.

The alkalis can be used singly or as a mixture of two or more thereof. The alkali can be used after mixing with water.

In both Method 1, Method 2 and Method 3, phosgene may be introduced in a vapor state or introduced in a liquid state under pressure. It is also possible to introduce phosgene dissolved in the organic solvent.

An introducing inlet of phosgene may be at the vapor phase part or liquid phase part of the reactor. When the introducing inlet is at the liquid phase, isatoic anhydrides are sometimes deposited to close the introducing inlet. Therefore, the reaction must be carried out taking this point into consideration.

An amount of phosgene introduced is normally from about 0.9- to 2-fold molar amount, preferably from about 1- to 1.7-fold molar amount, with respect to the anthranilic acids.

It is preferred that, firstly, a predetermined amount of phosgene was introduced while maintaining the pH of the reaction mixture at 2 to 10, and, then, remaining phosgene or a mineral acid such as hydrochloric acid is added thereto until the pH becomes 2 or lower, preferably 1 or lower, thereby making it possible to improve the yield of the objective product.

Thus, the objective isatoic anhydrides are produced. When isatoic anhydrides are removed from the reaction mixture, phosgene remained is normally exhausted in the first place. Examples of such a exhaustion process include a process of purging an inert gas such as nitrogen, a process of distilling off with a solvent, and a process of adding an alcohol such as methanol to react with phosgene. It is possible to obtain isatoic anhydrides by distilling off the organic solvent from the reaction mixture after exhaustion of phosgene, followed by subjecting to separating means such as filtration.

The isatoic anhydrides thus obtained can also be further purified, if necessary.

According to the present invention, Method 1, Method 2 and Method 3, it becomes possible to inhibit the formation of whipped cream mass from the reaction mixture and the volume efficiency of the reactor is improved, thereby remarkably improving the productivity. It becomes also possible to improve yield of isatoic anhydrides, the objective product.

The following Examples further illustrate the present invention in detail but are not to be construed to limit the scope thereof.

EXAMPLE 1

To a 200 ml flask equipped with a condenser (−20° C.), water (43.5 g), tetrahydrofuran (43.5 g) and 4-chloroanthranilic acid (4.38 g, purity: 98%) were charged. After cooling to 10° C. with stirring, sodium carbonate was added thereto so that the pH became 6 to 7. Then, the reaction was conducted while introducing phosgene in the vapor phase part of a reactor with a flow rate of 0.2 g/minute, cooling the reaction mixture so that the temperature was maintained at 20° to 25° C., and adding an aqueous 10% sodium carbonate so that the pH was maintained at 6 to 7.

After 3 g of phosgene has been introduced, the addition of the aqueous sodium carbonate was stopped and phosgene was further introduced continuously until the pH became 1. The maximum value of the volume of the reaction mixture was 180 ml.

After the completion of the reaction, the reaction mixture was heated to 65° C. and, after distilling off phosgene together with a part of the solvent, the resultant crystal was filtered, washed with methanol and then dried to obtain 4.4 g of 7-chloroisatoic anhydride (purity: 99%). The yield was 88%.

The volume efficiency (yield of the objective product per maximum volume 100 ml of the reaction mixture) was 2.4 g/100 ml.

EXAMPLE 2

To a 2 liter flask equipped with a condenser (−20° C.), water (510 g), tetrahydrofuran (51 g) and 4-chloroanthranilic acid (106 g, purity: 98%) were charged. After cooling to 10° C. with stirring, an aqueous 23% sodium hydroxide was added thereto so that the pH became 6 to 7. Then, the reaction was conducted while introducing phosgene in a vapor phase part of a reactor with a flow rate of 0.5 g/minute, cooling the reaction mixture so that the temperature was maintained at 5° to 15° C. and adding an aqueous 23% sodium hydroxide so that the pH was maintained at 6 to 7.

After 67 g of phosgene has been introduced, the addition of the aqueous sodium hydroxide was stopped and phosgene was further introduced continuously until the pH became 1. The maximum value of the volume of the reaction mixture was 1100 ml.

According to the same manner as in Example 1, the reaction mixture was post-treated to obtain 116 g of 7-chloroisatoic anhydride (purity: 99%). The yield was 97% and the volume efficiency was 10.5 g/100 ml.

Comparative Example 1

According to the same manner as in Example 1 except that the volume of the flask was changed to 1 liter and water (87 g) was used in place of water and tetrahydrofuran, the reaction was conducted. The maximum value of the volume of the reaction mixture was 350 ml.

According to the same manner as in Example 1, the reaction mixture was post-treated to obtain 4.12 g of 7-chloroisatoic anhydride (purity: 99%). The yield was 83% and the volume efficiency was 1.2 g/100 ml.

EXAMPLE 3

Into a 200 ml flask equipped with a cooling apparatus (−20° C.) were placed 53 g of water, 2.8 g of laurylpyridinium chloride and 18 g of 4-chloroanthranilic acid (purity: 98%). The mixture was cooled to 10° C. with stirring and adjusted to pH 6–7 with addition of an aqueous sodium hydroxide. Then, the reaction was conducted while introducing phosgene into the vapor phase part of the reactor at a flow rate of 0.3 g/minute, cooling the reaction mixture so as to maintain the temperature at 5°–15° C. and adding an aqueous sodium hydroxide such that pH was maintained at 6–7.

When 23 g of phosgene was introduced, addition of the aqueous sodium hydroxide was stopped and introduction of phosgene was further continued until pH became 1.

After completion of the reaction, excess phosgene was exhausted by addition of methanol and crystals were filtered, washed with methanol and dried to give 18.5 g of 7-chloroisatoic anhydride (purity: 98%). The conversion of 4-chloroanthranilic acid was 98% and the yield was 91%.

The volume efficiency (yield of the objective product per maximum volume 100 ml the reaction mixture) was 10 g/100 ml.

EXAMPLE 4

According to the same manner as in Example 3, except that 17 g of toluene and 2.9 g of laurylpyridinium chloride were used in place of 2.8 g of laurylpyridinium chloride and the flow rate of phosgene introduced was changed to 0.2 g/minute, 19.6 g of 7-chloroisatoic anhydride (purity: 99.7%) was obtained.

The conversion of 4-chloroanthranilic acid was 100%, the yield was 91% and the volume efficiency was 12 g/100 ml.

Comparative Example 2

According to the same manner as in Example 3, except that the flask was changed to 1 l flask, 88 g of water was added in place of water and laurylpyridinium chloride, an aqueous sodium carbonate was used in place of the aqueous sodium hydroxide and phosgene was changed to 5.2 g, 4.1 g of 7-chloroisatoic anhydride (purity: 99%) was obtained.

The conversion of 4-chloroanthranilic acid was 83%, the yield was 20% and the volume efficiency was 1.2 g/100 ml.

Comparative Example 3

The same manner Example 3 was conducted, except that phosgene was introduced without addition of laurylpyridinium chloride. The reaction mixture became a whipped cream mass with an increase in volume, thereby blocking the cooling apparatus. Therefore, the reaction was stopped when about 10 g of phosgene was introduced.

The conversion of 4-chloroanthranilic acid was 33%.

Comparative Example 4

According to the same manner as in Example 4, except that the flask was changed to 300 ml flask, laurylpyridinium chloride was not used, 103 g of water was added, and that amounts of toluene, phosgene and 4-chloroanthranilic acid were changed to 34 g, 40 g and 35 g, respectively, 35.6 g of 7-chloroisatoic anhydride (purity: 73.8%) was obtained. The yield was 67% and the volume efficiency was 9 g/100 ml.

Comparative Example 5

According to the same manner as in Example 3 except that laurylpyridinium chloride was replaced by 1.7 g of sodium laurylbenzene sulfonate and the amount of phosgene was changed to 30 g, 7-chloroisatoic anhydride was obtained.

The conversion of 4-chloroanthranilic acid was 69% and the yield was 64%.

Comparative Example 6

According to the same manner as in Example 3, except that laurylpyridinium chloride was replaced by 2.28 g of benzyl triethyl ammonium chloride and the amount of phosgene was changed to 30 g, 7-chloroisatoic anhydride was obtained.

The conversion of 4-chloroanthranilic acid was 73%.

EXAMPLE 5

To a 200 ml flask equipped with a condenser (−20° C.), water (78.9 g), tetrahydrofuran (315.5 g) and 4,5-dimethoxyanthranilic acid (80.5 g, purity: 98%) were charged. After cooling to 20° C. with stirring, an aqueous 25% sodium hydroxide solution was added thereto so that the pH became 6 to 7. Then, the reaction was conducted while introducing phosgene in the vapor phase part of a reactor with a flow rate of 0.26 g/minute, cooling the reaction mixture so that the temperature was maintained at 15° to 25° C., and adding an aqueous 25% sodium hydroxide solution so that the pH was maintained at 6 to 7.

After 47.5 g of phosgene has been introduced, the addition of the aqueous sodium hydroxide and phosgene was stopped and 18 % hydrochloric acid (11.7 g) was added so that the pH became 1.

According to the same manner as that in Example 3, a post treatment was carried out to obtain 79.6 g of 6,7-dimethoxyisatoic anhydride (purity: 88%). The yield was 83%.

EXAMPLE 6

According to the same manner as in Example 5, except that 171.6 g of water and 171.6 g of toluene were used in place of 78.9 g of water and 315.5 g of tetrahydrofuran, and that 4-chloroanthranilic acid was used in place of 4,5-dimethoxyanthranilic acid, 80.9 g of $^7$-chloroisatoic anhydride (purity: 91 %) was obtained.

The yield was 93%.

EXAMPLE 7

According to the sa manner as in Example 3, except that the flask was changed to 500 ml flask, 70 g of water, 280 g of toluene and 35 g of 4-chloroanthranilic acid were in place of 53 g of water and 2.8 g of laurylpyridinium chloride, and that the reaction temperature was maintained at 15°–25° C., 41.0 g of 7-chloroisatoic anhydride (purity: 94%) was obtained.

The yield was 98%.

What is claimed is:

1. A process for producing an isatoic anhydride compound represented by the formula (II)

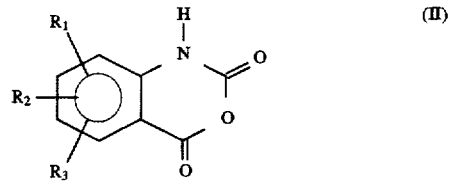

wherein $R_1$ and $R_2$ each represent a hydrogen atom, a halogen atom, a nitro group, a lower alkyl group which is optionally substituted with a halogen atom, an aralkyl group which is optionally substituted with a halogen atom, an alkoxy group which is optionally substituted with a halogen atom, an alkoxycarbonyl group which is optionally substituted with a halogen atom, an acyloxy group or $XNR_4R_5$ (wherein X is a direct bond, a lower alkylene group or a carbonyl group provided that, when X is a direct bond or a lower alkylene group, $R_4$ and $R_5$ each represent a lower alkyl group or N, $R_4$ and $R_5$ may form a five- or six-membered heterocycle which optionally contain another hetero atom and, when X is a carbonyl group, $R_4$ and $R_5$ each represent a hydrogen atom or a lower alkyl group or N, $R_4$ and $R_5$ may form a five- or six-membered heterocycle which optionally contain another hetero atom and further, when containing another hetero atom, said hetero atom may be substituted); and $R_3$ is a hydrogen atom, a lower alkyl group which is optionally substituted with a halogen atom, an aralkyl group which is optionally substituted with a halogen atom, an alkoxy group which is optionally substituted with a halogen atom or an alkoxycarbonyl group which is optionally substituted with a halogen atom, which comprises the step of reacting phosgene with an anthranilic acid compound represented by the formula (I)

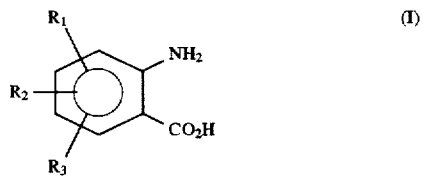
(I)

wherein $R_1$ $R_2$ and $R_3$ are as defined above, or a salt thereof in the presence of an alkylpyridium salt in an aqueous solvent.

2. The process according to claim 1, in which the alkylpyridinium salt is a compound represented by the formula (III)

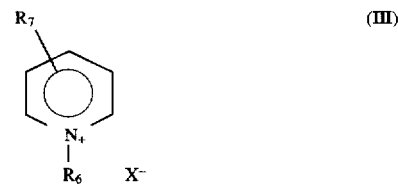
(III)

wherein $R_6$ represents an alkyl group having 8–20 carbon atoms, $R_7$ represents a hydrogen atom or a lower alkyl group and X an anion.

3. The process according to claim 1 wherein the amount of the alkylpyridinium salt is in a range of 0.005–0.5 fold by weight with respect to the amount of anthranilic acid compound of the formula (I) and a salt thereof.

4. The process according to claim 1 wherein the amount of the alkylpyridinium salt is in a range of 0.01–0.2 fold by weight with respect to the amount of anthranilic acid compound of the formula (I) and a salt thereof.

5. The process according to claim 1 wherein the amount of the alkylpyridinium salt is in a range of 0.05–0.2 fold by weight with resect to the amount of anthranilic acid compound of the formula (I) and a salt thereof.

* * * * *